United States Patent
Zirnstein et al.

(10) Patent No.: US 6,365,637 B1
(45) Date of Patent: Apr. 2, 2002

(54) USE OF ESTERS OR AMIDES OF HYDROXYLATED CARBOXYLIC ACIDS AS SOLUBILIZERS

(75) Inventors: Michael Zirnstein, Schriesheim; Folker Ruchatz, Neustadt; Karl Kolter, Limburgerhof; Knut Oppenländer, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/433,548

(22) Filed: Nov. 4, 1999

(30) Foreign Application Priority Data

Nov. 10, 1998 (DE) .......................... 198 51 777

(51) Int. Cl.$^7$ ............................ C07C 69/66; A61K 6/00
(52) U.S. Cl. ................. 514/943; 560/185; 560/187; 560/189; 424/401
(58) Field of Search ................. 510/185, 187, 510/189; 514/943; 424/401

(56) References Cited

U.S. PATENT DOCUMENTS

| | | |
|---|---|---|
| 3,776,857 A | 12/1973 | Lindner |
| 4,366,151 A | 12/1982 | Oppenlaender et al. |
| 5,710,207 A | 1/1998 | Moeller et al. |

FOREIGN PATENT DOCUMENTS

| | | |
|---|---|---|
| DE | 4331228 | 3/1995 |
| EP | 017059 | 10/1980 |
| FR | 2056177 | 7/1969 |
| JP | 9069135 | 12/1991 |

OTHER PUBLICATIONS

Lorenz et al., Agents and Actions, vol. 12, ½(1982).

*Primary Examiner*—Paul J. Killos
(74) *Attorney, Agent, or Firm*—Keil & Weinkauf

(57) ABSTRACT

The use of esters or amides of hydroxylated carboxylic acids as solubilizers, particularly for pharmaceutical, cosmetic and food preparations, is described.

18 Claims, No Drawings

USE OF ESTERS OR AMIDES OF HYDROXYLATED CARBOXYLIC ACIDS AS SOLUBILIZERS

The invention relates to the use of esters or amides of hydroxylated carboxylic acids as solubilizer.

In the manufacture of homogeneous pharmaceutical or cosmetic preparations, the solubilization of hydrophobic substances has achieved very great practical importance.

Solubilization is taken to mean an improvement in the solubility by virtue of surface-active compounds which can convert substances which are insoluble or virtually insoluble in water into clear, at most opalescent aqueous solutions without changing the chemical structure of these substances in the process.

The solubilizates formed are notable for the fact that the substance which is insoluble or virtually insoluble in water is present in dissolved form in the molecular associations of the surface-active compounds which form in aqueous solution, also called micelles. The resulting solutions are stable single-phase systems which appear optically clear to opalescent and can be prepared without the input of a great deal of energy.

Solubilizers can improve the appearance, for example, of cosmetic formulations and food preparations by making the formulations transparent. Furthermore, in the case of pharmaceutical preparations, the bioavailability and thus the activity of medicaments can also be increased by using solubilizers.

The principal solubilizers used for pharmaceutical medicaments and cosmetic active ingredients are the following products:

ethoxylated (hydrogenated) castor oil, (e.g. Cremophor® products, BASF);

ethoxylated sorbitan fatty acid esters, (e.g. Tween® products, ICI);

ethoxylated hydroxystearic acid, (e.g. Solutol® products, BASF).

The above-described hitherto used solubilizers do, however, exhibit a number of technical disadvantages.

For example, their parenteral application, is associated with the release of histamine and a consequent drop in blood pressure (Lorenz et al., Agents and Actions, Vol. 12, 1/2 , 1982).

The known solubilizers have only a low solubilizing action for some virtually insoluble medicaments, such as, for example, clotrimazole.

Surface-active compounds frequently have high hemolytic activity, which prevents use in the pharmaceutical field, in particular in substances administered parenterally.

EP-A-0 017 059 describes the preparation of alkoxylated fatty acids of the Solutol® type and their use as solubilizers. However, solubilizers having this type of structure display the above disadvantages.

DE-A-4 331 228 describes the reaction of polyethylene glycol with hydroxycarboxylic acids and the use of these reaction products as antifoams for aqueous systems.

J5 9069135 describes the use of polyoxyalkylene esters of ricinoleic acid as emulsifier. The compounds disclosed here have the disadvantage that they are either insufficiently soluble in water or, upon parenteral application, cause an undesirably high release of histamine.

FR 2056177 describes water-in-oil emulsions containing alkoxylated fatty acids as emulsifiers.

It is an object of the present invention to provide novel solubilizers for pharmaceutical, cosmetic and food preparations which do not have the abovementioned disadvantages.

We have found that this object is achieved by the use of esters or amides of hydroxylated carboxylic acids of the formula I

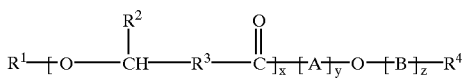

in which the substituents and variables independently of one another have the following meanings:

$R^1$ is hydrogen, $C_1$–$C_{22}$-acyl,

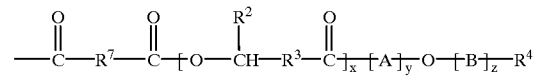

$R^2$ is hydrogen, $C_1$–$C_{16}$-alkyl, $C_2$–$C_{12}$-alkenyl;
$R^3$ is $C_1$–$C_{16}$-alkylene, $C_2$–$C_{16}$-alkenylene;
$R^4$ is $C_1$–$C_{12}$-alkyl, $C_2$–$C_{12}$-alkenyl, $C_1$–$C_{12}$-acyl;
A is —N($R^5$)—$R^6$—;
B is —$CH_2$—$CH_2$—O—, —$CH_2$—$CH_2$—$CH_2$—O— and/or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl, $[B]_z$—$R^4$;
$R^6$ is —$CH_2$—$CH_2$—, —$CH_2$—$CH_2$—$CH_2$—, —CH($CH_3$)—$CH_2$—;
$R^7$ is $C_1$–$C_{16}$-alkylene, $C_2$–$C_{16}$-alkenylene, radical of a dimerized fatty acid;
x is 1 to 6;
y is 0 or 1;
z is 8 to 18 as solubilizers.

Alkyl radicals $R^2$ which may be mentioned are branched or unbranched $C_1$–$C_{16}$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl and n-hexadecyl.

Alkyl radicals $R^4$ and $R^5$ which may be mentioned are branched or unbranched $C_1$–$C_{12}$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl and n-dodecyl.

Alkenyl radicals $R^2$ and also $R^4$ and $R^5$ which may be mentioned are branched or unbranched $C_2$–$C_{12}$-alkenyl chains, for example vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Alkylene radicals $R^3$ and $R^7$ which may be mentioned are branched or unbranched $C_1-C_{16}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, n-tridecylene, n-tetradecylene, n-pentadecylene and n-hexadecylene.

Alkenyl radicals $R^3$ and $R^7$ which may be mentioned are branched or unbranched $C_2-C_{16}$-alkenyl chains, for example vinylene, propenylene, isopropenylene, 1-butenylene, 2-butenylene, 1-pentenylene, 2-pentenylene, 2-methyl-1-butenylene, 2-methyl-2-butenylene, 3-methyl-1-butenylene, 1-hexenylene, 2-hexenylene, 1-heptenylene, 2-heptenylene, 1-octenylene, 2-octenylene, 1-nonenylene, 1-decenylene, 1-undecenylene, 1-dodecenylene, 1-tridecenylene, 1-tetradecenylene, 1-pentadecenylene or 1-hexadecenylene.

Acyl radicals $R^1$ which may be mentioned are branched or unbranched, saturated or unsaturated, optionally hydroxylated $C_1-C_{22}$-acyl radicals or $C_1-C_{21}$-alkylcarbonyl radicals, for example formyl, methylcarbonyl (acetyl), hydroxymethylcarbonyl, ethylcarbonyl, 1-hydroxyethylcarbonyl, n-propylcarbonyl, 3-hydroxypropylcarbonyl, n-butylcarbonyl, 1-methylpropylcarbonyl, 2-methylpropylcarbonyl, 1,1-dimethylethylcarbonyl, n-pentylcarbonyl, 5-hydroxypentylcarbonyl, 3-methylbutylcarbonyl, 2,2-dimethylpropylcarbonyl, n-hexylcarbonyl, n-heptylcarbonyl, n-octylcarbonyl, 2-ethylhexylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl and n-eicosylcarbonyl.

Acyl radicals $R^4$ and $R^5$ which may be mentioned are branched or unbranched, saturated or unsaturated, optionally hydroxylated $C_1-C_{12}$-acyl radicals or $C_1-C_{11}$-alkylcarbonyl radicals, for example formyl, methylcarbonyl (acetyl), hydroxymethylcarbonyl, ethylcarbonyl, 1-hydroxyethylcarbonyl, n-propylcarbonyl, 3-hydroxypropylcarbonyl, n-butylcarbonyl, 1-methylpropylcarbonyl, 2-methylpropylcarbonyl, 1,1-dimethylethylcarbonyl, n-pentylcarbonyl, 5-hydroxypentylcarbonyl, 3-methylbutylcarbonyl, 2,2-dimethylpropylcarbonyl, n-hexylcarbonyl, n-heptylcarbonyl, n-octylcarbonyl, 2-ethylhexylcarbonyl, n-nonylcarbonyl, n-decylcarbonyl and n-undecylcarbonyl.

Dimerized fatty acids are taken to mean saturated or unsaturated fatty acids having from 12 to 44 carbon atoms, preferably from 32 to 40 carbon atoms, which are prepared by dimerization of one or different unsaturated fatty acids.

The dimerizable fatty acids are mono- or polyunsaturated compounds with a carbon chain having from 6 to 22 carbon atoms, preferably from 12 to 22 carbon atoms, particularly preferably from 16 to 20 carbon atoms, and mixtures of these fatty acids or fatty alcohols, for example oleic acid/linoleic acid mixtures.

The dimerized fatty acids essentially contain linear and cyclic compounds which can be unsaturated or hydrogenated, but which are preferably hydrogenated.

Examples of unsaturated dimer fatty acid structures:

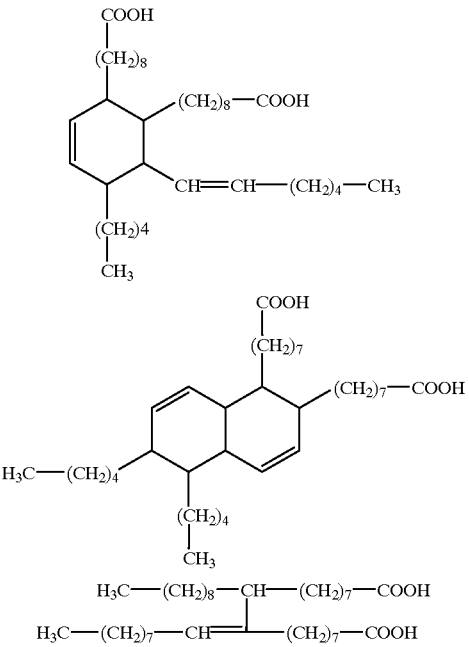

Suitable dimerized fatty acids are preferably the products which are obtainable commercially under the name Pripol® (Unichema) or Empol® (Henkel). These dimerized oleic acid/linoleic acid mixtures comprise mainly linear and cyclic compounds. In addition, these products may also comprise fractions of monomeric and of trimeric and more highly condensed fatty acids.

Typical commercially available dimeric fatty acids have the following approximate composition:

| Monomeric acids: | 0–15% by weight, |
|---|---|
| dimeric acids: | 50–99 % by weight, |
| tri- and more highly polymerized acids: | 1–35% by weight, | it being possible for the content to vary within these limits depending on the origin of the monomers, the polymerization process and the work-up process.

Hydroxylated carboxylic acids are, for example, taken to mean monohydroxycarboxylic acids which can be saturated or unsaturated.

Monohydroxycarboxylic acids include, for example, 12-hydroxystearic acid and ricinoleic acid, and also glycolic acid, lactic acid, 4-hydroxybutyric acid, 5-hydroxypentanoic acid, 6-hydroxyhexanoic acid, 10-hydroxydecanoic acid, 11-hydroxyundecanoic acid, and hydroxy fatty acids, which are obtainable by hydrogenation of epoxy fatty acids having from 16 to 22 carbon atoms. Mixtures of said hydroxycarboxylic acids are also suitable.

Saturated monohydroxycarboxylic acids having at least 9 carbon atoms are preferable. Particular preference is given to 12-hydroxystearic acid.

It is also possible to use dihydroxycarboxylic acids (also in mixtures with monohydroxycarboxylic acids), which are obtainable from epoxy fatty acids having from 12 to 22 carbon atoms by hydrolytic ring opening, for example 9,10-dihydroxystearic acid.

Advantageous solubilizers are esters of hydroxylated carboxylic acids of the formula I in which the substituents independently of one another have the following meanings:

$R^1$ is hydrogen, $C_1$–$C_{22}$-acyl,

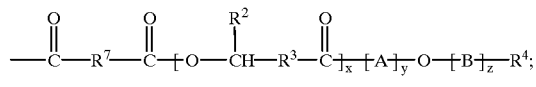

$R^2$ is hydrogen, $C_1$–$C_{12}$-alkyl;
$R^3$ is $C_1$–$C_{12}$-alkylene, $C_2$–$C_{12}$-alkenylene;
$R^4$ is $C_1$–$C_4$-alkyl;
$R^7$ is $C_1$–$C_6$-alkylene, radical of a dimerized fatty acid;
B is —$CH_2$—$CH_2$—O— and/or —$CH(CH_3)$—$CH_2$—O—;
x is 1 to 3;
y is 0;
z is 10 to 18.

Preferred solubilizers are esters of hydroxylated carboxylic acids of the formula I in which the substituents independently of one another have the following meanings:

$R^1$ is hydrogen, $C_1$–$C_{22}$-acyl,

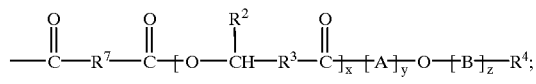

$R^2$ is $C_1$–$C_{12}$-alkyl;
$R^3$ is $C_1$–$C_{12}$-alkylene;
$R^4$ is $C_1$–$C_4$-alkyl;
$R^7$ is $C_1$–$C_6$-alkylene, radical of a dimerized fatty acid;
B is —$CH_2$—$CH_2$—O—;
x is 1 to 3;
y is 0;
z is 10 to 18.

Particularly preferred solubilizers are esters of hydroxylated carboxylic acids of the formula I in which the substituents independently of one another have the following meanings:

$R^1$ is hydrogen, $C_{12}$–$C_{22}$-acyl,

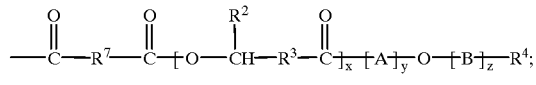

$R^2$ is $C_1$–$C_9$-alkyl;
$R^3$ is $C_6$–$C_{12}$-alkylene;
$R^4$ is methyl, ethyl;
$R^7$ is a radical of a dimerized fatty acid;
B is —$CH_2$—$CH_2$—O—;
x is 1 to 2;
y is 0;
z is 10 to 18.

Very particularly preferred solubilizers are esters of 12-hydroxystearic acid of the formula II

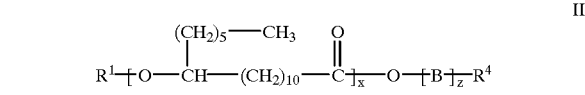

in which the substituents independently of one another have the following meanings:

$R^1$ is hydrogen, $C_1$–$C_{22}$-acyl,

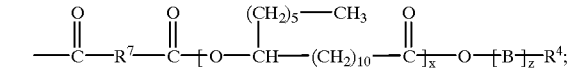

$R^4$ is methyl;
$R^7$ is a radical of a dimerized fatty acid;
B is —$CH_2$—$CH_2$—O—;
x is 1 to 2;
z is 10 to 18.

For the condensation with the hydroxylated carboxylic acids, in particular with 12-hydroxystearic acid, the following hydrophilic compounds are suitable:

$C_1$–$C_{12}$-alkyl-, $C_2$–$C_{12}$-alkenyl- or $C_1$–$C_{12}$-acylpolyalkylene glycols, in particular $C_1$–$C_{12}$-alkyl-, $C_2$–$C_{12}$-alkenyl- or $C_1$–$C_{12}$-acylpolyethylene glycols and $C_1$–$C_{12}$-alkyl-, $C_2$–$C_{12}$-alkenyl- or $C_1$–$C_{12}$-acylpolypropylene glycols having from 8 to 18 monomer units; these are taken to mean polyalkylene glycols, in particular polyethylene glycols or polypropylene glycols, which are capped at one end, advantageously methylpolyethylene glycol, ethylpolyethylene glycol and/or propylpolyethylene glycol, particularly preferably methyl- and/or ethylpolyethylene glycol, very particularly preferably methylpolyethylene glycol having an (average) molecular weight of from 370 to 1000 g/mol, preferably from 450 to 800 g/mol. The alkyl, alkenyl or acyl radicals here correspond to the definitions already given for the substituent $R^4$ in formula I.

As well as the aforementioned homopolymers, it is also possible to react corresponding copolymers capped at one end, including those consisting of ethylene glycol and propylene glycol units of varying composition, with the hydroxylated carboxylic acids.

The aforementioned polyethylene glycols or polypropylene glycols which are capped at one end can additionally be aminated, for example O-(1-aminoethyl-2) methylpolyethylene glycols or O-(1-aminopropyl-3) methylpolyethylene glycols, which can be prepared by amination or aminopropylation from the abovementioned alkylpolyethylene glycols.

The OH groups of the hydroxylated carboxylic acids used according to the invention can be unprotected or acylated.

Suitable acyl radicals are the $C_1$–$C_{22}$-acyl groups already specified for the substituent $R^1$ in formula I. These can optionally also be hydroxylated.

Of the shorter chain acyl radicals, the radicals of the following $C_1$–$C_6$-carboxylic acids may be mentioned advantageously: formic acid, acetic acid, propionic acid, caproic acid, cyclohexanoic acid; particularly preferably acetic acid and caproic acid; very particularly preferably caproic acid.

Of the longer chain acyl radicals, the radicals of the following $C_7$–$C_{22}$-carboxylic acids may be mentioned advantageously: caprylic acid, oenanthic acid, capric acid, lauric acid, stearic acid, oleic acid, behenic acid; particularly preferably stearic acid.

In the case of hydroxylated acyl radicals, particular mention may be made of the radicals of 12-hydroxystearic acid, ricinoleic acid, 6-hydroxyhexanoic acid, particularly preferably 12-hydroxystearic acid.

Suitable dihydroxyacyl radicals which may be mentioned are 9,10-dihydroxystearic acid radicals.

The suitable trihydroxyacyl radicals include 9,10,12-trihydroxystearic acid radicals.

The OH groups of the hydroxylated carboxylic acids used according to the invention can also be bonded to dicarboxylic acids. Suitable dicarboxylic acids include aliphatic dicarboxylic acids, aromatic dicarboxylic acids and the dimer fatty acids already mentioned in the introduction (polymerized fatty acids).

Suitable aliphatic dicarboxylic acids are, for example, $C_3$-$C_{14}$-dicarboxylic acids, such as malonic acid, succinic acid, fumaric acid, maleic acid, glutaric acid, adipic acid, pimelic acid, suberic acid, azelaic acid, sebacic acid, cyclohexane-1,4-dicarboxylic acid.

Aromatic dicarboxylic acids are, for example, phthalic acid, isophthalic acid or terephthalic acid.

The linking of the hydrophilic compounds with 12-hydroxystearic acid is via ester bonds or, in the case of the aminated polyalkylene glycols capped at one end, via amide bonds, preference being given to the ester bonds.

The 12-hydroxystearic esters which are used in preference can be prepared by processes known per se by condensation of 12-hydroxystearic acid with the aforementioned hydrophilic compounds.

It is also possible to use hydroxystearic esters such as, for example, methyl ester, ethyl ester, or corresponding lactones for the transesterification.

It is likewise possible to use corresponding acid chlorides or anhydrides (including mixed anhydrides).

Thus, 12-hydroxystearic acid or, where appropriate, a carboxylic acid mixture consisting of 12-hydroxystearic acid and additionally one or more of the abovementioned carboxylic acids can be condensed in a "one pot process" with the hydrophilic compound to give the 12-hydroxystearic acid derivatives according to the invention.

If, in addition to 12-hydroxystearic acid, one or more of the abovedescribed carboxylic acids are additionally used, the molar ratio of 12-hydroxystearic acid to the other carboxylic acids is in the range from 0.5 to 1 to 10 to 1, preferably in the range from 1 to 1 to 4 to 1.

In contrast to the "one pot process", it is also possible to firstly prepare a precondensate of hydroxystearic acid or of hydroxystearic acid and the other carboxylic acids, and then to carry out the condensation with the hydrophilic polyalkylene compound.

It is also possible to firstly prepare a precondensate from hydroxystearic acid and the hydrophilic compound which can then be reacted with the other carboxylic acid.

The condensation can be carried out using an acidic or a basic catalyst or without additional catalyst.

Suitable acidic catalysts are Brönstedt acids and Lewis acids, for example sulfuric acid, p-toluenesulfonic acid, hydrochloric acid, phosphoric acid, hypophosphorus acid, phosphoric acid, methanesulfonic acid, boric acid, aluminum chloride, boron trifluoride, tetraethyl orthotitanate, tin dioxide, tin butyldilaurate and mixtures thereof. Preference is given to hypophosphorus acid, phosphorus acid, phosphoric acid, p-toluenesulfonic acid and binary mixtures thereof.

Suitable basic catalysts are sodium methoxide, sodium ethoxide, potassium carbonate, sodium carbonate, calcium carbonate, magnesium carbonate, potassium tert-butoxide, potassium hydroxide, sodium hydroxide, lithium hydroxide, magnesium oxide, potassium phosphate, sodium borohydride.

The catalyst is used here in amounts of from 0.05 to 10% by weight, preferably from 0.1 to 5% by weight, based on the starting materials.

The reaction can be carried out in solvents or solvent-free. The solvent-free procedure is preferred. Suitable solvents are, for example, toluene, xylene, acetonitrile, N,N-dimethylformamide, N,N-dimethylacetamide, N-methylpyrrolidone, diglyme, dimethylethylene glycol, tetrahydrofuran, dioxane, ethylene carbonate, propylene carbonate.

When the reaction has finished or during the reaction the solvent can be distilled off.

The condensation is usually carried out at pressures of from 5 mbar to atmospheric pressure and at temperatures of from 60 to 220° C., preferably from 120 to 180° C., particularly preferably at from 130 to 170° C.; where a 12-hydroxystearic ester is used as starting material, at from 30 to 220° C., preferably from 60 to 170° C. The reaction times are from 2 to 25 hours. The reaction is monitored by means of the amount of removed water of reaction or by determining the acid number or, in the case of a 12-hydroxystearic ester as starting material, by means of the amount of alcohol in question.

Compounds of the structure Ib

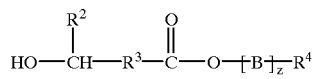

Ib in which the substituents $R^2$ to $R^4$ and the group $[B]_z$ have the meanings already given in the introduction, can be prepared by targeted protective group synthesis in which, by targeted blocking of the OH group of the hydroxylated carboxylic acids, a self-condensation to dimers, trimers and other oligomers in the subsequent esterification step with the polyalkylene glycol derivatives capped at one end is prevented.

In a particular embodiment, for example, the 12-hydroxyl group of the 12-hydroxystearic acid can, as THP ether, be protected from esterification. This can take place by reacting pure methyl 12-hydroxystearate with dihydropyran with p-toluenesulfonic acid catalysis. The methyl 12—O—tetrahydropyranyl-12-hydroxystearate formed can then be hydrolyzed to give the corresponding carboxylic acid. Subsequent esterification of the 12—O—tetra-hydropyranyl-12-hydroxystearic acid, for example with methylpolyglycols, can be carried out in a manner known per se inter alia with catalysis of dimethylaminopyridine (DMAP) using dicyclohexylcarbodiimide (DCC). Elimination of the THP protective group gives 12-hydroxystearic acid methylpolyethylene glycol monoesters which are free from oligomeric stearic acid fractions.

Suitable protective groups are all protective groups for hydroxyl functions which can be introduced as far as possible without secondary reactions, in particular largely without self-esterification of the 12-hydroxystearic acid or its derivatives, which are sufficiently stable under the chosen esterification conditions and which can again be eliminated when esterification has taken place, while avoiding ester cleavage.

Suitable protective groups for hydroxyl functions are known to the person skilled in the art and are described, for example, by T. W. Greene, P. G. M. Wuts in "Protective Groups in Organic Synthesis", Second Edition, p.14–118, John Wiley Sons, Inc. (1991). These protective groups include those which react with the hydroxyl group with ether formation. These are, for example, the methyl, methoxymethyl, tetrahydropyranyl, 2,2,2-trichloroethyl, t-butyl, allyl, benzyl and p-methoxybenzyl protective groups; silyl protective groups such as the trimethylsilyl, triisopropylsilyl and t-butyldimethylsilyl protective groups.

Suitable protective groups are also those which react with the hydroxyl group with ester formation. These include acetate, chloroacetate, trichloroacetate, methylcarbonate, benzylcarbonate.

Preferred protective groups are the tetrahydropyranyl and the benzyl protective groups.

Applications

The present invention makes available water-soluble amphiphilic compounds for use as solubilizers for pharmaceutical and cosmetic preparations and also for food preparations. They have the ability to solubilize virtually insoluble active ingredients in the field of pharmaceuticals and cosmetics, virtually insoluble food supplements, for example vitamins and carotenoids, but also virtually insoluble active ingredients for use in crop-protection compositions and also active ingredients for use in veterinary medicine in aqueous systems.

Surprisingly, the claimed compounds have been found to have good solubilization power for pharmaceutical and cosmetic active ingredients. In addition, the claimed compounds permit applications which are notable for a very low hemolysis rate, and a compatibility free from side effects following parenteral, oral and topical application to skin and mucosa. In particular, the compounds do not have side effects caused by interactions with blood corpuscle membranes. Following parenteral application there is no, or only a slight, release of histamine. Because of their low molecular weight, the solubilizers are able to pass through the kidneys.

In addition, it is expected that a "multi-drug-resistance-reversal" can be achieved with the carboxylic acid derivatives used according to the invention in the pharmaceutical application.

Solubilizers for Cosmetics

The compounds of the formula I can be used as solubilizers in cosmetic formulations. They are particularly suitable as solubilizers for cosmetic oils. They have good solubilizing power for fats and oils, such as groundnut oil, jojoba oil, coconut oil, almond oil, olive oil, palm oil, castor oil, soybean oil or wheatgerm oil, or for essential oils, such as dwarf pine oil, lavender oil, rosemary oil, spruce needle oil, pine needle oil, eucalyptus oil, peppermint oil, sage oil, bergamot oil, terpentine oil, melissa oil, juniper oil, lemon oil, aniseed oil, cardamon oil, camphor oil, etc. or for mixtures of these oils.

In addition, the compounds of the formula I according to the invention can be used as solubilizers for UV absorbers which are insoluble or virtually insoluble in water, such as, for example, 2-hydroxy-4-methoxy-benzophenone (Uvinul® M 40, BASF), 2,2',4,4'-tetrahydroxybenzophenone (Uvinul® D 50), 2,2'-dihydroxy-4,4,-dimethoxybenzophenone (Uvinul® D49), 2,4-dihydroxybenzophenone (Uvinul® 400), 2'-ethylhexyl 2-cyano-3,3-diphenylacrylate (Uvinul® N 539), 2,4,6-trianilino-p-(carbo-2'-ethylhexyl-1'-oxy)-1,3,5-triazine (Uvinul® T 150), 3-(4-methoxybenzylidene)camphor (Eusolex® 6300, Merck), 2-ethylhexyl N,N-dimethyl-4-aminobenzoate (Eusolex® 6007), 3,3,5-trimethylcyclohexyl salicylate, 4-isopropyl-dibenzoylmethane (Eusolex® 8020), 2-ethylhexyl p-methoxycinnamate and 2-isoamyl p-methoxycinnamate and mixtures thereof.

The present invention thus also provides cosmetic preparations which comprise at least one of the compounds of the formula I as solubilizers. Preference is given to those preparations which, in addition to the solubilizer, comprise one or more virtually insoluble cosmetic active ingredients, for example the abovementioned oils or UV absorbers.

These formulations are solubilizates based on water or water/alcohol. The compound I is used as solubilizer in a ratio of from 0.2:1 to 50:1, preferably from 0:5:1 to 20:1, particularly preferably from 1:1 to 15:1, very particularly preferably from 2:1 to 12:1 relative to the virtually insoluble cosmetic active ingredient.

The content of solubilizer according to the invention in the cosmetic preparation is, depending on the active ingredient, in the range from 1 to 50% by weight, preferably from 3 to 40% by weight, particularly preferably from 5 to 30% by weight.

In addition, it is possible to add other auxiliaries to this formulation, for example nonionic, cationic or anionic surfactants, such as alkyl polyglycosides, fatty alcohol sulfates, fatty alcohol sulfonates, fatty alcohol ether sulfates, fatty alcohol ether sulfonates, alkanesulfonates, fatty alcohol ethoxylates, fatty alcohol phosphates, alkylbetaines, sorbitan esters, POE-sorbitan esters, sugar fatty acid esters, fatty acid polyglyceryl esters, fatty acid partial glycerides, fatty acid carboxylates, fatty alcohol sulfosuccinates, fatty acid sarcosinates, fatty acid isethionates, fatty acid taurinates, citric acid esters, silicone copolymers, fatty acid polyglycol esters, fatty acid amides, fatty acid alkanolamides, quaternary ammonium compounds, alkylphenol ethoxylates, fatty amine ethoxylates, cosolvents, such as ethylene glycol, propylene glycol, glycerol etc.

Other constituents which may be added are natural or synthetic compounds, for example lanolin derivatives, cholesterol derivatives, isopropyl myristate, isopropyl palmitate, electrolytes, dyes, preservatives, acids (e.g. lactic acid, citric acid).

These formulations can be used, for example, in bath preparations such as bath oils, shaving lotions, face lotions, mouthwashes, hair lotions, eau de cologne, eau de toilette etc.

Description of the Solubilization Method

In the preparation of the solubilizates for cosmetic formulations, the compounds of the formula I can be used as 100% strength substance or as aqueous solution.

The solubilizer is usually dissolved in water and thoroughly mixed, for example using a magnetic stirrer, with the virtually insoluble cosmetic active ingredient to be used in each case, e.g. the abovementioned essential oils or perfume oils.

It is, however, also possible to dissolve the virtually insoluble cosmetic active ingredient to be used in a melt of the solubilizer and then to add demineralized water with continuous stirring.

Solubilizers for Pharmaceutical Applications

The claimed compounds are likewise suitable for use as solubilizer in pharmaceutical preparations of any type which are distinguished by the fact that they comprise one or more medicaments or vitamins or carotenoids which are insoluble or virtually insoluble in water. In particular, these are aqueous solutions or solubilizates for oral or parenteral application, such as, for example, injection solutions for intravenous, intramuscular or subcutaneous or intraperitoneal application.

Furthermore, the claimed compounds are suitable for use in oral presentations such as tablets, capsules, powders and solutions. In this case they are able to make available the virtually insoluble medicament with increased bioavailability.

For parenteral application, as well as solubilizates, it is also possible to use emulsions, for example fatty emulsions. For this purpose too, the claimed compounds are suitable for processing a virtually insoluble medicament.

Pharmaceutical formulations of the above type can be obtained by processing the claimed compounds with pharmaceutical active ingredients by traditional methods and using known and novel active ingredients.

The use according to the invention can additionally include pharmaceutical auxiliaries and/or diluents. Specific auxiliaries are cosolvents, stabilizers and preservatives.

The pharmaceutical active ingredients used are substances which have low or zero solubility in water. According to DAB 9 (German Pharmacopeia), the grading of the solubility of pharmaceutical active ingredients is as follows: slightly soluble (soluble in from 30 to 100 parts of solvent); sparingly soluble (soluble in from 100 to 1000 parts of solvent); virtually insoluble (soluble in more than 10,000 parts of solvent). The active ingredients can be from any of the indicated ranges.

Examples thereof which may be mentioned are benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, agents for treating Parkinson's disease and other antihyperkinetic agents, ophthalmics, neuropathy preparations, calcium metabolic regulators, muscle relaxants, narcotics, antilipemics, hepatic therapeutic agents, coronary agents, cardiacs, immunotherapeutics, regulatory peptides and their inhibitors, hypnotics, sedatives, gynecological agents, gout remedies, fibrinolytic agents, enzyme preparations and transport proteins, enzyme inhibitors, emetics, circulation-promoting agents, diuretics, diagnostics, corticoids, cholinergenics, bile duct therapeutics, antiasthmatics, broncholytics, betareceptor blockers, calcium antagonists, ACE inhibitors, arteriosclerotics, antiphlogistics, anticoagulants, antihypotonics, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents.

The novel compounds are used as solubilizers in pharmaceutical preparations by, for example, dispersing or dissolving the active ingredient in the solubilizer, optionally with warming, and mixing it with water while stirring.

Another preparation variant involves dissolving the solubilizer in the aqueous phase, optionally with slight warming, and subsequently dissolving the active ingredient in the aqueous solubilizer solution. The simultaneous dissolution of solubilizer and active ingredient in the aqueous phase is likewise possible.

The invention thus also provides pharmaceutical preparations which comprise at least one of the compounds of the formula I as solubilizers. Preference is given to preparations which, in addition to the solubilizer, comprise a pharmaceutical active ingredient which is insoluble or virtually insoluble in water, for example from the abovementioned indication fields.

Of the abovementioned pharmaceutical preparations, particular preference is given to those which are formulations which are administered parenterally.

The content of solubilizer according to the invention in the pharmaceutical preparation is, depending on the active ingredient, in the range from 1 to 50% by weight, preferably from 3 to 40% by weight, particularly preferably from 5 to 30% by weight.

Solubilizers for Food Preparations

As well as use in cosmetics and pharmaceuticals, the compounds of the formula I according to the invention are also suitable as solubilizers in the food sector for nutrients, auxiliaries or additives which are insoluble or virtually insoluble in water, such as, for example, fat-soluble vitamins or carotenoids. Examples which may be mentioned are clear drinks colored with carotenoids.

The invention thus also provides food preparations which comprise at least one of the compounds of the formula I as solubilizers. Preference is given to those preparations which, in addition to the solubilizer, comprise a vitamin or carotenoid which is insoluble or virtually insoluble in water.

Solubilizers for Crop-protection Preparations

The use of the compounds of the formula I according to the invention as solubilizers in agrochemistry can, inter alia, include formulations which comprise pesticides, herbicides, fungicides or insecticides, especially also preparations of crop-protection agents which are used as spray or pouring mixtures.

The invention further provides esters of hydroxylated carboxylic acids of the formula Ia

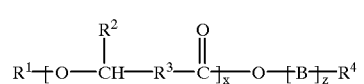

in which the substituents and variables independently of one another have the following meanings:

$R^1$ is hydrogen, $C_{12}$–$C_{22}$-acyl,

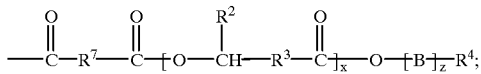

$R^2$ is $C_1$–$C_9$-alkyl;

$R^3$ is $C_6$–$C_{12}$-alkylene;

$R^4$ is methyl, ethyl;

$R^7$ is a radical of a dimerized fatty acid;

B is —$CH_2$—$CH_2$—O—;

x is 1 to 2;

z is 10 to 18.

Alkyl radicals $R^2$ which may be mentioned are branched or unbranched $C_1$–$C_9$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl and n-nonyl.

Alkylene radicals $R^3$ which may be mentioned are branched or unbranched $C_6$–$C_{12}$-alkylene chains, preferably n-hexylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene and n-dodecylene.

Acyl radicals $R^1$ which may be mentioned are branched or unbranched, saturated or unsaturated, optionally hydroxylated $C_{12}$–$C_{22}$-acyl radicals or $C_{11}$–$C_{21}$-alkylcarbonyl radicals, for example n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl and n-eicosylcarbonyl.

Preference is given to esters of hydroxylated carboxylic acids of the formula Ia in which the substituents and variables independently of one another have the following meanings:

$R^1$ is hydrogen;
$R^2$ is $C_6$–$C_9$-alkyl;
$R^3$ is $C_9$–$C_{12}$-alkylene;
$R^4$ is methyl;
B is —$CH_2$—$CH_2$—O—;
x is 1 to 2;
z is 10 to 18.

Very particular preference is given to esters of 12-hydroxystearic acid of the formula II

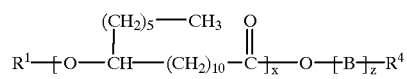

in which the substituents and variables independently of one another have the following meanings:

$R^1$ is hydrogen, $C_{12}$–$C_{22}$-acyl,

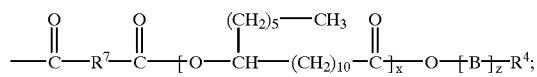

$R^4$ is methyl;
$R^7$ is a radical of a dimerized fatty acid;
B is —$CH_2$—$CH_2$—O—;
x is 1 to 2;
z is 10 to 18.

The examples below further illustrate the preparation of the polymerized fatty acid derivatives and their use as solubilizers.

A) Preparation of the Esters of Hydroxylated Carboxylic Acids used According to the Invention

EXAMPLE 1

12-Hydroxystearic acid methylpolyethylene glycol (500) monoester a) Methyl 12-hydroxystearate 268 g of HCl gas were passed with stirring over the course of 1 h into a solution of 2200 g of about 89% strength 12-hydroxystearic acid [Edenor® OSSG, Henkel; corresponding to about 1960 g (6.52 mol) of pure 12-HS] in 6000 ml of methanol at 40° C. The temperature rose to 50° C. The mixture was then stirred at 50° C. for 2 h. Most of the HCl gas was removed by subsequently introducing nitrogen. The methanol was distilled off on a rotary evaporator under reduced pressure. Fractional crystallization from acetone and subsequent drying gives a total of 573 g (1.82 mol; 27.9% yield) of methyl 12-hydroxystearate having a melting point of 58° C. and a purity of 98.2% (content according to GC).

b) Methyl 12—O—tetrahydropyranylstearate

A solution of 500 g (1.59 mol) of methyl 12-hydroxystearate and 1.20 g of p-toluenesulfonic acid in 3500 ml of $CH_2Cl_2$ was cooled to 0–5° C. At this temperature, 135 g (1.60 mmol) of 3,4-dihydro-2H-pyran, dissolved in 250 ml of $CH_2Cl_2$, were metered in with stirring over the course of 2.5 h. At 2–5° C., the mixture was stirred for a total of 2.5 h, 1.35 g (1.6 mmol) of 3,4-dihydro-2H-pyran being added after 1.5 h, and 0.1 g of p-toluenesulfonic acid being added after 2 h. 2 g of $K_2CO_3$ were then added in the form of a concentrated aqueous solution and the mixture was briefly stirred. The organic phase was washed twice with water, twice with dilute ammonia and a further time with water. After the organic phase had been dried with sodium sulfate, the $CH_2Cl_2$ was distilled off at 25° C. under reduced pressure on a rotary evaporator. Yield (crude): 655 g of a pale yellow oil.

Each 130 g of the crude product were dissolved in 200 ml of n-hexane and applied to a 4-L frit filled with 1300 g of silica gel. Elution was carried out in each case using about 4 liters of n-hexane and about 6 liters of n-hexane/methyl t-butyl ether. The fractions in which pure methyl 12—O—THP-12-hydroxystearate was detected were combined and evaporated to dryness on a rotary evaporator to give a total of 557.6 g (1.40 mol, 88%) of a colorless oil.

1H-NMR spectrum: 270 MHz, $CDCl_3$, δ=0.90 (t, 3H; $CH_3$—$CH_2$—), 1.1–1.95 (m, 34H), 2.31 (t, 2H; —$CH_2$—$CO_2CH_3$), 3.42–3.53 (m, 1H), 3.55–3.64 (m, 1H; —$CH_2$—CH(—O—THP)—$CH_2$—), 3.68 (s, 3H; —$CO_2CH_3$), 3.86–3.98 (m, 1H), 4.65 (m, 1H; O—CH—O).

c) 12—O—Tetrahydropyranylstearic acid

A solution of 100.0 g (0.251 mol) of methyl 12—O—THP-stearate and 28.2 g (0.503 mol) of KOH in a solvent mixture, comprising 120 ml of dioxane and 100 ml of water, was heated to 85° C. with stirring. After 1.5 h, the reaction mixture was cooled to room temperature in an ice bath. A saturated, aqueous citric acid solution was carefully added to adjust the pH to 4.5. The aqueous solution was then extracted with 3×about 100 ml of $CH_2Cl_2$. The solvent was removed under reduced pressure on a rotary evaporator at room temperature. Yield: 95.7 g (0.248 mol, 98.8%) of a viscous, colorless oil.

1H-NMR spectrum: 270 MHz, $CDCl_3$, δ=0.90 (t, 3H; $CH_3$—$CH_2$—), 1.1–1.95 (m, 34H), 2.34 (t, 2H; —$CH_2$—$CO_2H$), 3.42–3.57 (m, 1H), 3.58–3.64 (m, 1H; —$CH_2$—CH(—O—THP)—$CH_2$—), 3.85–3.98 (m, 1H), 4.65 (m, 1H; O—CH—O), 10.8–11.2 (br. s, 1H; —$CO_2H$).

d) 12-O-Tetrahydropyranylstearic acid methylpolyethylene glycol (500) monoester 3.05 g (25.0 mmol) of 4-dimethylaminopyridine was added to a solution, prepared at room temperature, of 80.0 g (208 mmol) of 12—O—THP-stearic acid in 80 g of $CH_2Cl_2$. After the mixture had been cooled to from −3 to +5° C. using ice/common salt bath, 51.6 g (250 mmol) of dicyclohexylcarbodiimide as a 50% strength solution in $CH_2Cl_2$ were added dropwise over the course of one hour at this temperature, and the mixture was then stirred for 20 minutes. 104.2 g (208 mmol) of methylpolyethylene glycol 500 (Pluriol® A 500 E, BASF) were added dropwise as a 50% strength solution in $CH_2Cl_2$ over the course of one hour at 0° C. After a post-stirring time of 20 hours, the dicyclohexylurea which had precipitated out was filtered off with suction and the filtrate was washed with 2× about 100 ml of an aqueous NaCl solution acidified to pH 3 using hydrochloric acid. The organic phase was dried with $Na_2SO_4$ and the solvent was removed on a rotary evaporator. Yield: 178.3 g of a colorless, waxy substance.

1H-NMR spectrum: 270 MHz, $CDCl_3$, δ=0.90 (t, 3H; $CH_3$—$CH_2$—), 1.1–1.95 (m, 34H), 2.32 (t, 2H; —$CH_2$—$CO_2$—$CH_2CH_2O$—), 3.37 (s, 3H, $CH_3$—O—), 3.43–3.53 (m, 1H), 3.55–3.70 (m, ca. 47H; —$CH_2$—O—$CH_2CH_2O$—), 3.85–3.98 (m, 1H), 4.22 (t, 2H; —$CO_2$—$CH_2CH_2O$—), 4.64 (m, 1H; O—CH—O).

e) 12-Hydroxystearic acid methylpolyethylene glycol (500) monoester 170 g (196 mmol) of 12—O—THP-stearic acid methylpolyethylene glycol (500) monoester were dissolved in 380 ml of an ethanol/water/isopropanol (45:45:10) mixture and a pH of 2–3 was adjusted by adding concentrated hydrochloric acid. The mixture was stirred initially for 12 h at 45° C. and then left to stand overnight at room temperature. The mixture was neutralized using $K_2CO_3$ and evaporated to dryness on a rotary evaporator. Crude yield: about 130 g (about 85%) of a colorless, waxy substance. The crude product was then purified by column chromatography to give a colorless wax with a melting point of 38–41° C. Yield: 64%.

1H-NMR spectrum: 400 MHz, $CDCl_3$, δ=0.88 (t, $^3J$=7.0 Hz, 3H; $CH_3$—$CH_2$—), 1.3–1.4 (m, 26H; alkylene-H), 1.62 (m, 2H; alkylene-H) 2.32 (t, $^3J$=7.5 Hz, 2H; —$CH_2$—$CO_2$—$CH_2CH_2O$—), 3.38 (s, 3H; $CH_3$—$OCH_2CH_2O$—), 3.54–3.70 (m, ca. 48H; —$CH_2$—O—$CH_2CH_2O$—), 4.22 (t, $^3J$=4.8 Hz, 2H; —$CO_2$—$CH_2CH_2O$—).

1H-NMR spectrum: 400 MHz, $CDCl_3$, [derivatization with trichloroacetyl isocyanate (TAI)], δ=0.88 (t, $^3J$=7.0 Hz, 3H; $CH_3$—$CH_2$—), 1.3 (m, 22H; alkylene-H), 1.6 (m, 6H; alkylene-H), 2.32 (t, $^3J$=7.6 Hz, 2H; —$CH_2$—$CO_2$—$CH_2CH_2O$—), 3.37 (s, 3H; $CH_3$—$OCH_2CH_2O$—), 3.55–3.70 (m, ca. 47H; —$CH_2$—O—$CH_2CH_2O$—), 4.21 (t, $^3J$=4.9 Hz, 2H; —$CO_2$—$CH_2CH_2O$—), 4.94 (quint., $^3J$=6.2 Hz, 1H; TAI—O—CH($CH_2$—)$_2$).

The $^1$H-NMR spectrum does not have any signals for a hydroxymethine group esterified with fatty acid at δ=4.90 ppm. Esterification of 12-hydroxystearic acid units with one another has thus not taken place.

EXAMPLE 2

12-Hydroxystearic Acid Methylpolyethylene Glycol (750) Monoester

The preparation was carried out by a method similar to the synthesis sequence a) to e) in Example 1. In step d), methylpolyethylene glycol 750 (Pluriol® A 750 E) was used instead of methylpolyethylene glycol 500.

EXAMPLE 3

12-Hydroxystearic Acid Methylpolyethylene Glycol (900) Monoester

The preparation was carried out by a method similar to the synthesis sequence a) to e) in Example 1. In step d), methylpolyethylene glycol 900 was used instead of methylpolyethylene glycol 500.

EXAMPLE 4

Esterification of 12-hydroxystearic Acid with Methylpolyethylene Glycol 470 (molar ratio 1:1)

At 80° C., 96.6 g of methylpolyethylene glycol 470 (OH number=122 mg of KOH/g) and 1.60 g of 50% strength hypophosphorous acid were added to 63.0 g of 12-hydroxystearic acid (Edenort OSSG, Henkel, acid number (AN)=181 mg of KOH/g), and the mixture was stirred for 20 h at 160° C. under protective gas. The water of reaction which formed was distilled off.

Yield 152.2 g

Acid number (AN): 6.3 mg of KOH/g; OH number (OHN): 58 mg of KOH/g; saponification value (SV): 92 mg of KOH/g.

EXAMPLE 5

Esterification of 12-hydroxystearic Acid with Methylpolyethylene Glycol 500 (molar ratio 1:1)

At 80° C., 100.0 g of methylpolyethylene glycol 500 (Pluriol® A 500 E, BASF; OHN=109 mg of KOH/g) and 1.60 g of 50% strength hypophosphorous acid were added to 60.0 g of 12-hydroxystearic acid (Edenor® OSSG, Henkel, AN=181 mg of KOH/g), and the mixture was stirred for 20 h at 160° C. under protective gas. The water of reaction which formed was distilled off.

Yield 152 g

Acid number (AN): 6.9 mg of KOH/g; OH number (OHN): 54 mg of KOH/g; saponification value (SV): 89 mg of KOH/g;

EXAMPLE 6

Esterification of 12-hydroxystearic Acid with Methylpolyethylene Glycol 750 (molar ratio 1:1)

At 80° C., 218.7 g of methylpolyethylene glycol 750 (Pluriol® A 750 E, BASF; OHN=77.0 mg of KOH/g) and 3.10 g of 50% strength hypophosphorous acid were added to 90.0 g of 12-hydroxystearic acid (Edenor® OSSG, Henkel), and the mixture was stirred for 21 h at 180° C. under protective gas. The water of reaction which formed was distilled off.

Yield 303 g

AN: 3.6 mg of KOH/g; OHN: 43 mg of KOH/g; SV: 60 mg of KOH/g.

EXAMPLE 7

Esterification of 12-hydroxystearic Acid with a Mixture of Methylpolyethylene Glycol 500 and Methylpolyethylene Glycol 750 (molar ratio 1.5:0.6:0.4)

At 80° C., 51.0 g of methylpolyethylene glycol 500 (Pluriol® A 500 E, BASF; OHN=112 mg of KOH/g) and 51.0 g of methylpolyethylene glycol 750 (Pluriol® A 750 E, BASF; OHN=77.0 mg of KOH/g) were added to 79.1 g of 12-hydroxystearic acid (Edenor® OSSG, Henkel, AN=181 mg of KOH/g). After 1.81 g of 50% strength hypophosphorous acid had been added, the mixture was stirred for 20 h at 165° C. under protective gas. The water of reaction which formed was distilled off.

Yield 172.7 g
AN: 7.8 mg of KOH/g; OHN: 33 mg of KOH/g; SV: 91 mg of KOH/g.

EXAMPLE 8

Esterification of 12-hydroxystearic Acid with a Mixture of Methylpolyethylene Glycol 500 and Methylpolyethylene Glycol 750 (molar ratio 2:0.6:0.4)

At 80° C., 45.0 g of methylpolyethylene glycol 500 (Pluriol® A 500 E, BASF; OHN=109 mg of KOH/g) and 45.0 g of methylpolyethylene glycol 750 (Pluriol® A 750 E, BASF; OHN=77.0 mg of KOH/g) were added to 93.0 g of 12-hydroxystearic acid (Edenor® OSSG, Henkel, AN=181 mg of KOH/g). After 1.83 g of 50% strength hypophosphorous acid had been added, the mixture was stirred for 20 h at 165° C. under protective gas. The water of reaction which formed was distilled off.

Yield 173.8 g
N: 9.3 mg of KOH/g; OHN: 28 mg of KOH/g; SV: 105 mg of KOH/g.

EXAMPLE 9

Esterification of 12-hydroxystearic Acid with Methylpolyethylene Glycol 900 (molar ratio 1:1)

At 80° C., 117.0 g of methylpolyethylene glycol 900 (OHN=62 mg of KOH/g) and 1.56 g of 50% strength hypophosphorous acid were added to 39.0 g of 12-hydroxystearic acid (Edenor® OSSG, Henkel), and the mixture was stirred for 20 h at 160° C. under protective gas. The water of reaction which formed was distilled off.

Yield 150 g
AN: 5.9 mg of KOH/g; OHN: 36 mg of KOH/g; SV: 60 mg of KOH/g.

EXAMPLE 10

Esterification of 12-hydroxystearic Acid with Methylpolyethylene Glycol 900 (molar ratio 2:1)

At 80° C., 1.50 g of 50% strength hypophosphorous acid were added to a melt of 90.0 g of methylpolyethylene glycol 900 (OHN=62 mg of KOH/g). After the mixture had been heated to 165° C. under protective gas, 60.0 g of a 12-hydroxystearic acid melt (Edenor® OSSG, Henkel), heated to about 90° C., were added dropwise with stirring over the course of 8 h. The temperature was slowly increased to 180° C. The mixture was stirred for a further 20 h at 180° C. The water of reaction which formed was distilled off.

Yield 137 g
AN: 5.7 mg of KOH/g; OHN: 40 mg of KOH/g; SV: 81 mg of KOH/g.

EXAMPLE 11

Esterification of 12-hydroxystearic Acid with Methylpolyethylene Glycol 1300 (molar ratio 1:1)

At 80° C., 195 g of methylpolyethylene glycol 1300 (OHN=44 mg of KOH/g) and 2.4 g of 50% strength hypophosphorous acid were added to 45.0 g of 12-hydroxystearic acid (Edenor® OSSG, Henkel), and the mixture was stirred for 6 h at 170° C. under protective gas. The water of reaction which formed was distilled off. The temperature was increased to 180° C. for a further 4 h. After the mixture had cooled to 80° C., 12.3 g each of aluminum oxide and Ambosol and 0.6 g of Hyflow were added, and the mixture was stirred for 1 h at 80° C. and filtered while hot through a pressure filter.

Yield 221.6 g
AN: 2.2 mg of KOH/g.

EXAMPLE 12

Esterification of a Mixture of Dimer Fatty Acid and 12-hydroxystearic Acid with Methylpolyethylene Glycol 500 (molar ratio 1:0.9:2.1)

At 80° C., 101.6 g of methylpolyethylene glycol 500 (Pluriol A 500 E, BASF, OHN=109 mg of KOH/g) and 1.78 g of 50% strength hypophosphorous acid were added to a mixture of 29.0 g of 12-hydroxystearic acid (Edenor OSSG, Henkel) and 47.6 g of dimer fatty acid (Pripol 1009, Unichema, AN=193 mg of KOH/g), and the mixture was stirred for 20 h at 170° C. under protective gas. The water of reaction which formed was filtered off.

Yield 163.9 g
AN: 9.7 mg of KOH/g; OHN: 9 mg of KOH/g; SV: 92 mg of KOH/g.

EXAMPLE 13a (precursor of Example 13b and 13c)

Esterification of 12-hydroxystearic Acid with Dimer Fatty Acid (molar ratio 1:0.9)

At 80° C., 107.5 g (Pripol® 1009, Unichema, AN=193 mg of KOH/g) and 1.73 g of 50% strength hypophosphorous acid were added to 63.5 g of 12-hydroxystearic acid (Edenor® OSSG, Henkel), and the mixture was stirred for 14.5 h at 170° C. under protective gas. The water of reaction which formed was distilled off.

Yield 166 g
AN: 139 mg of KOH/g; OHN: 3 mg of KOH/g; SV: 202 mg of KOH/g.

EXAMPLE 13b

Esterification of a Mixture of Dimer Fatty Acid and 12-hydroxystearic Acid with Methylpolyethylene Glycol 500 (molar ratio 1:0.9:2.1)

At 80° C., 74.0 g of methylpolyethylene glycol 500 (Pluriol® A 500 E, BASF, OHN=109 mg of KOH/g) and 1.28 g of 50% strength hypophosphorous acid were added to 54.5 g of the precondensate from Example 13a, and the mixture was stirred for 12 h at 170° C. under protective gas. The water of reaction which formed was distilled off.

Yield 121.5 g
AN: 7.7 mg of KOH/g; OHN: 6 mg of KOH/g; SV: 94 mg of KOH/g.

EXAMPLE 13c

Esterification of a Mixture of Dimer Fatty Acid and 12-hydroxystearic Acid with Methylpolyethylene Glycol 900 (molar ratio 1:0.9:2)

At 80° C., 94.3 g of methylpolyethylene glycol 900 (OHN=62 mg of KOH/g) and 1.36 g of 50% strength hypophosphorous acid were added to 41.3 g of the precondensate from Example 13a, and the mixture was stirred for 20 h at 170° C. under protective gas. The water of reaction which formed was distilled off.

Yield 128.1 g
AN: 6.7 mg of KOH/g; OHN: 4 mg of KOH/g; SV: 68 mg of KOH/g.

EXAMPLE 14

Esterification of a Mixture of Stearic Acid and 12-hydroxystearic Acid with Methylpolyethylene Glycol 900 (molar ratio 0.75:1:0.95)

At 80–90° C., 106.3 g of methylpolyethylene glycol 900 (OHN=62 mg of KOH/g) and 1.72 g of 50% strength hypophosphorous acid were added to a melt consisting of 26.9 g of stearic acid (Edenor C18 98/100, Henkel; AN=200 mg of KOH/g) and 38.8 g of 12-hydroxystearic acid (Edenor OSSG, Henkel), and the mixture was stirred for 20 h at 180° C. under protective gas. The water of reaction which formed was distilled off.

Yield 163.6 g
AN: 12.3 mg of KOH/g; OHN: 8 mg of KOH/g; SV: 78 mg of KOH/g.

EXAMPLE 15a (precursor for Example 15b)

Esterification of 12-hydroxystearic Acid with Lauric Acid (molar ratio 1:0.75)

At 80° C., 59.2 g of lauric acid and 1.79 g of 50% strength hypophosphorous acid were added to 120.0 g of 12-hydroxystearic acid (Edenort® OSSG, Henkel), and the mixture was stirred for 4 h at 165–170° C. under protective gas. The water of reaction which formed was distilled off.

Yield 172.6 g
AN: 118.4 mg of KOH/g; OHN: 8 mg of KOH/g; SV: 229 mg of KOH/g.

EXAMPLE 15b

Esterification of 12-hydroxystearic Acid with Lauric Acid and with Methylpolyethylene Glycol 900 (molar ratio 1:0.75:0.9)

At 80°C., 71.0 g of methylpolyethylene glycol 900 (OHN=62 mg of KOH/g) and 1.10 g of 50% strength hypophosphorous acid were added to 39.4 g of the precondensate from Example 15a, and the mixture was stirred for 20 h at 170–180° C. under protective gas. The water of reaction which formed was distilled off.

Yield 102 g
AN: 7.9 mg of KOH/g; OHN: 5 mg of KOH/g; SV: 69 mg of KOH/g.

EXAMPLE 16

Esterification of a Mixture of Lauric Acid and 12-hydroxystearic Acid with Methylpolyethylene Glycol 1300 (molar ratio 0.75:1:1)

At 80° C., 114.9 g of methylpolyethylene glycol 1300 (OHN=44 mg of KOH/g) were added to a mixture of 28.4 g of 12-hydroxystearic acid (Edenor OSSG, Henkel), 14.0 g of lauric acid and 1.60 g of 50% strength hypophosphorous acid, and the mixture was stirred for 25 h at 170° C. under protective gas. The water of reaction which formed was distilled off.

Yield 143 g
AN: 6.8 mg of KOH/g; OHN: 22 mg of KOH/g; SV: 65 mg of KOH/g.

EXAMPLE 17

Esterification of a Mixture of Lauric Acid and 12-hydroxystearic Acid with Methylpolyethylene Glycol 1300 (molar ratio 0.45:1:0.65)

At 80° C., 102.6 g of methylpolyethylene glycol 1300 (OHN=44 mg of KOH/g) and 1.50 g of 50% strength hypophosphorous acid were added to a mixture of 38.0 g of 12-hydroxystearic acid (Edenor OSSG, Henkel) and 11.5 g of lauric acid, and the mixture was stirred for 21 h at 165–180° C. under protective gas. The water of reaction which formed was distilled off.

Yield 141 g
AN: 8.7 mg of KOH/g; OHN: 9 mg of KOH/g; SV: 75 mg of KOH/g.

B) Pharmaceutical and cosmetic formulations

EXAMPLE 18

Diazepam Injection Solution 400 mg of 12-hydroxystearic acid MPG-500 ester 1:1 (prepared as in Example 5) were dissolved in 1578 mg of double-distilled water. 10 mg of diazepam were then added to the solubilizer solution and stirred until the medicament had dissolved. The solution was preserved using 2 mg of sodium disulfite and 10 mg of benzyl alcohol and sterilized by filtration using customary methods and poured into injection vials.

EXAMPLE 19

17-β-Estradiol Gelatine Capsules 100 mg of 17-β-estradiol were mixed with 10 g of 12-hydroxystearic acid MPG-500 ester 1:1 (prepared as in Example 5) and 80 g of molten PEG 6000 and 10 g of ethanol, and the mixture was then transferred directly in liquid form to capsules.

EXAMPLE 20

Oral Cyclosporine Formulation (liquid-filled capsule)

100 g of cyclosporine A were dissolved in 770 g of 12-hydroxystearic acid MPG-500 ester 1:1 (prepared as in Example 5), 100 ml of ethanol and 75 ml of propylene glycol, and the viscous, clear solution was then transferred to capsules. This solution was infinitely dilutable with water.

EXAMPLE 21

Diazepam Emulsion for Parenteral Application 160 g of 12-hydroxystearic acid MPG-500 ester 1:1 (prepared as in Example 5) were dissolved in 660 g of doubly distilled water. The diazepam (10 g) was dispersed in a 1:1 mixture of soya oil and Miglyol oil (oil phase is 200 g). In addition, 10 g of soya lecithin were used, which was dissolved in the oil phase. The two phases were predispersed and then emulsified by high-pressure homogenization.

EXAMPLE 22

17-β-Estradiol Tablets 10 g of 17-β-3-estradiol were melted with 50 g of 12-hydroxystearic acid MPG-500 ester 1:1 (prepared as in Example 5). The melt was drawn to 940 g of Ludipress. The granules were then mixed with 0.5 g of magnesium stearate and subsequently tableted.

EXAMPLE 23

Diazepam-containing Powder

Diazepam and 12-hydroxystearic acid MPG-500 ester 1:1 (prepared as in Example 5) as solubilizer were dissolved in ethanol. Sorbitol was then added as carrier and likewise dissolved. The solvent was removed and the mixture was dried under reduced pressure.

EXAMPLE 24

Sunscreen 25 g of 12-hydroxystearic acid MPG-500 ester 1:1 (prepared as in Example 5) were melted at about 60° C., and 2.5 g of Uvinul T 150 were dissolved in the melt. A mixture, heated to 60° C., of 62.5 g of doubly distilled water and 10 g of glycerol was then carefully added dropwise with stirring. This gave a clear solution, which was cooled to room temperature and then transferred to a suitable container.

C) Application Examples

EXAMPLE 25

Solubilizing Action using 17-β-estradiol, Sulfathiazole and Clotrimazole as Examples 20% strength solubilizer solutions were used. The esters of the hydroxylated carboxylic acids were melted with gentle heating (temp. to 65° C.), and the medicament was added to the melt. The phosphate buffer pH 7.0 (USP XXIII) was then added in small amounts. The mixture was stirred at room temperature until the saturation concentration of the medicament was reached.

| Compound | Sulfa-thiazole | 17-β-Estra-diol | Clotrim-azole |
|---|---|---|---|
| Phosphate buffer pH 7.0 | 0.07 | 0.0 | 0.0 |
| Sorbitan fatty acid ester (Tween ® 80) | 0.7 | 0.09 | 0.03 |
| Ethoxylated castor oil (Cremophor ® EL) | 0.7 | 0.06 | 0.01 |
| 12-Hydroxystearic acid MPG 500 ester (Example 5) | 0.43 | 0.35 | 0.18 |
| 12-Hydroxystearic acid MPG 470 ester (Example 4) | 0.44 | 0.36 | 0.18 |
| 12-Hydroxystearic acid MPG 750 ester (Example 2) | 0.81 | 0.30 | 0.31 |
| 12-Hydroxystearic acid MPG 750 ester (Example 6) | 0.54 | 0.31 | 0.20 |
| 12-Hydroxystearic acid MPG 500 ester (Example 1) | 0.95 | 0.40 | 0.37 |

The figures refer to the amount of solubilized medicament in percent by weight.

EXAMPLE 26

Hemolysis Activity

The hemolytic activity of the claimed compounds was tested in a RBC (red blood cell) test on human erythrocytes. The incubation time was 60 min at room temperature. The low hemolytic activity of the 1% strength solutions is evident.

| Compound | Hemolysis of the 1% strength solutions in phosphate buffer[1] |
|---|---|
| Phosphate buffer pH 7.0 | 0% |
| Sorbitan fatty acid ester (Tween 80) | 4% |
| Solutol ® HS 15 | 1% |
| Ethoxylated castor oil (Cremophor ® EL) | 0% |
| 12-Hydroxystearic acid MPG 500 ester (Example 5) | 3% |
| 12-Hydroxystearic acid MPG 470 ester (Example 4) | 0% |
| 12-Hydroxystearic acid MPG 750 ester (Example 2) | 1% |
| 12-Hydroxystearic acid MPG 750 ester (Example 6) | 0% |
| 12-Hydroxystearic acid MPG 500 ester (Example 1) | 0% |

[1] The percentages refer to the photometric hemolysis values, based on the maximum values for wholly induced hemolysis.

EXAMPLE 27

Canine Tolerability

After intravenous injection of a 5% strength aqueous solution of the claimed compound into dogs, the histamine release in the blood was monitored. The claimed substances showed a lower increase in the histamine level in the blood than the known solubilizers:

| Compound | 5 min before application | 5 min after application | 15 min after application |
|---|---|---|---|
| 12-Hydroxystearic acid MPG 500 ester (Example 1) | 4 | 28 | 6 |
| 12-Hydroxystearic acid MPG 750 ester (Example 2) | 3 | 23 | 3 |
| 12-Hydroxystearic acid MPG 500 ester (Example 5) Comparative Example | 5 | 6 | 7 |
| Sorbitan fatty acid ester (Tween ® 80) | 3 | 14142 | 58065 |
| Solutol ® HS 15 | 5 | 138 | 220 |
| 12-Hydroxystearic acid MPG 900 ester (Example 3) | 4 | 5731 | 4682 |
| 12-Hydroxystearic acid MPG 900 ester (Example 9) | 7 | 1484 | 918 |
| 12-Hydroxystearic acid MPG 1300 ester (Example 11) | 10 | 11746 | 6774 |

The figures give the level of histamine in the blood in ng/ml.

We claim:

1. A method of solubilizing a component of an aqueous composition which comprises admixing with the composition an effective amount of at least one ester or amide of hydroxylated carboxylic acids of formula I

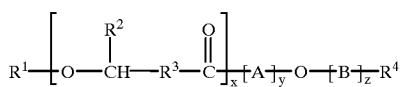

wherein the substituents and variables independently of one another have the following meanings:

$R^1$ is hydrogen, $C_1$–$C_{22}$-acyl or a moiety

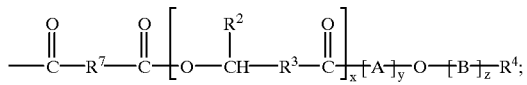

$R^2$ is hydrogen, $C_1$–$C_{16}$-alkyl or $C_2$–$C_{12}$-alkenyl;
$R^3$ is $C_1$–$C_{16}$-alkylene or $C_2$–$C_{16}$-alkenylene;
$R^4$ is $C_1$–$C_{12}$-alkyl, $C_2$–$C_{12}$-alkenyl or $C_1$–$C_{12}$-acyl;
A is —N($R^5$)—$R^6$—;
B is —$CH_2$—$CH_2$—O—, —$CH_2$—$CH_2$—$CH_2$—O— or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl or [B]$_z$—$R^4$;
$R^6$ is —$CH_2$—$CH_2$—, —$CH_2$—$CH_2$—$CH_2$— or —CH($CH_3$)—$CH_2$—;
$R^7$ is $C_1$–$C_{16}$-alkylene, $C_2$–$C_{16}$-alkenylene or a radical of a dimerized fatty acid;
x is 1 to 6, where the radicals $R^2$ and $R^3$ are identical or different when x is 2 to 6;
y is 0 or 1; and
z is 8 to 18, where the radicals B are identical or different, as solubilizer.

2. The method of claim 1, wherein
$R^1$ is hydrogen, $C_1$–$C_{22}$-acyl or a moiety

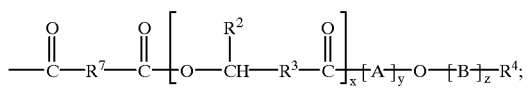

$R^2$ is hydrogen or $C_1$–$C_{12}$-alkyl;
$R^3$ is $C_1$–$C_{12}$-alkylene or $C_2$–$C_{12}$-alkenylene;
$R^4$ is $C_1$–$C_4$-alkyl;
$R^7$ is $C_1$–$C_6$-alkylene or a radical of a dimerized fatty acid;
B is —$CH_2$—$CH_2$—O— or —CH($CH_3$)—$CH_2$—O—;
x is 1 to 3, where the radicals $R^2$ and $R^3$ are identical or different when x is 2 or 3;
y is 0; and
z is 10 to 18, where the radicals B are identical or different.

3. The method of claim 1, wherein
$R^1$ is hydrogen, $C_1$–$C_{22}$-acyl or a moiety

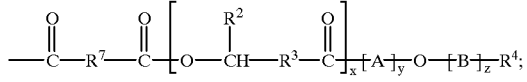

$R^2$ is $C_1$–$C_{12}$-alkyl;
$R^3$ is $C_1$–$C_{12}$-alkylene;
$R^4$ is $C_1$–$C_4$-alkyl;

$R^7$ is $C_1$–$C_6$-alkylene or a radical of a dimerized fatty acid;
B is —$CH_2$—$CH_2$—O—;
x is 1 to 3, where the radicals $R^2$ and $R^3$ are identical or different when x is 2 or 3;
y is 0;
z is 10 to 18, where the radicals B are identical or different.

4. The method of claim 1, wherein
$R^1$ is hydrogen, $C_{12}$–$C_{22}$-acyl or a moiety

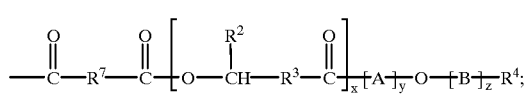

$R^2$ is $C_1$–$C_9$-alkyl;
$R^3$ is $C_6$–$C_{12}$-alkylene;
$R^4$ is methyl or ethyl;
$R^7$ is a radical of a dimerized fatty acid;
B is —$CH_2$—$CH_2$—O—;
x is 1 or 2, where the radicals $R^2$ and $R^3$ are identical or different when x is 2;
y is 0;
z is 10 to 18, where the radicals B are identical or different.

5. The method of claim 1, wherein formula I represents an ester of 12-hydroxystearic acid of formula II,

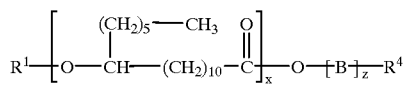

wherein the substituents and variables independently of one another have the following meanings:

$R^1$ is hydrogen, $C_{12}$–$C_{22}$-acyl or a moiety

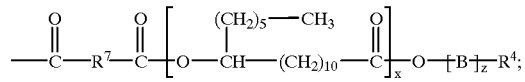

$R^4$ is methyl;
$R^7$ is a radical of a dimerized fatty acid;
B is —$CH_2$—$CH_2$—O—;
x is 1 or 2, where the radicals $R^2$ and $R^3$ are identical or different when x is 2;
z is 10 to 18, where the radicals B are identical or different.

6. The method of claim 1, wherein the aqueous composition is a pharmaceutical or a cosmetic composition.

7. The method of claim 1, wherein the aqueous composition is a food preparation.

8. A pharmaceutical composition comprising as solubilizer an effective amount of at least one hydroxylated carboxylic ester or amide of formula I

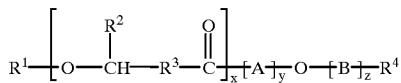

wherein the substituents and variables independently of one another have the following meanings:

$R^1$ is hydrogen, $C_1$–$C_{22}$-acyl or a moiety

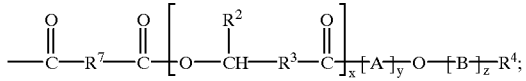

$R^2$ is hydrogen, $C_1$–$C_{16}$-alkyl or $C_2$–$C_{12}$-alkenyl;
$R^3$ is $C_1$–$C_{16}$-alkylene or $C_2$–$C_{16}$-alkenylene;
$R^4$ is $C_1$–$C_{12}$-alkyl, $C_2$–$C_{12}$-alkenyl or $C_1$–$C_{12}$-acyl;
A is —N($R^5$)—$R^6$—;
B is —$CH_2$—$CH_2$—O—, —$CH_2$—$CH_2$—$CH_2$—O— or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl or $[B]_z$—$R^4$;
$R^6$ is —$CH_2$—$CH_2$—, —$CH_2$—$CH_2$—$CH_2$— or —CH($CH_3$)—$CH_2$—;
$R^7$ is $C_1$–$C_{16}$-alkylene, $C_2$–$C_{16}$-alkenylene or a radical of a dimerized fatty acid;
x is 1 to 6, where the radicals $R^2$ and $R^3$ are identical or different when x is 2 to 6;
y is 0 or 1; and
z is 8 to 18, where the radicals B are identical or different.

9. The composition defined in claim 8, further comprising at least one pharmaceutical active ingredient which is insoluble or virtually insoluble in water.

10. The composition defined in claim 8, which is adapted for parenteral administration.

11. A cosmetic composition comprising as solubilizer an effective amount of at least one hydroxylated carboxylic ester or amide of formula I

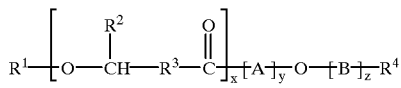

wherein the substituents and variables independently of one another have the following meanings:

$R^1$ is hydrogen, $C_1$–$C_{22}$-acyl or a moiety

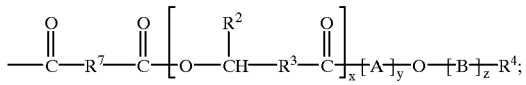

$R^2$ is hydrogen, $C_1$–$C_{16}$-alkyl or $C_2$–$C_{12}$-alkenyl;
$R^3$ is $C_1$–$C_{16}$-alkylene or $C_2$–$C_{16}$-alkenylene;
$R^4$ is $C_1$–$C_{12}$-alkyl, $C_2$–$C_{12}$-alkenyl or $C_1$–$C_{12}$-acyl;
A is —N($R^5$)—$R^6$—;
B is —$CH_2$—$CH_2$—O—, —$CH_2$—$CH_2$—$CH_2$—O— or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl or $[B]_z$—$R^4$;
$R^6$ is —$CH_2$—$CH_2$—, —$CH_2$—$CH_2$—$CH_2$— or —CH($CH_3$)—$CH_2$—;
$R^7$ is $C_1$–$C_{16}$-alkylene, $C_2$–$C_{16}$-alkenylene or a radical of a dimerized fatty acid;
x is 1 to 6, where the radicals $R^2$ and $R^3$ are identical or different when x is 2 to 6;
y is 0 or 1; and
z is 8 to 18, where the radicals B are identical or different.

12. The composition defined in claim 11, further comprising at least one cosmetic active ingredient which is insoluble or virtually insoluble in water.

13. A food composition comprising as a solubilizer an effective amount of at least one hydroxylated carboxylic ester or amide of formula I

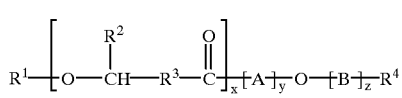

wherein the substituents and variables independently of one another have the following meanings:

$R^1$ is hydrogen, $C_1$–$C_{22}$-acyl or a moiety

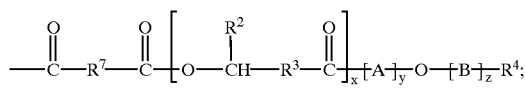

$R^2$ is hydrogen, $C_1$–$C_{16}$-alkyl or $C_2$–$C_{12}$-alkenyl;
$R^3$ is $C_1$–$C_{16}$-alkylene or $C_2$–$C_{16}$-alkenylene;
$R^4$ is $C_1$–$C_{12}$-alkyl, $C_2$–$C_{12}$-alkenyl or $C_1$–$C_{12}$-acyl;
A is —N($R^5$)—$R^6$—;
B is —$CH_2$—$CH_2$—O—, —$CH_2$—$CH_2$—$CH_2$—O— or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl or $[B]_z$—$R^4$;
$R^6$ is —$CH_2$—$CH_2$—, —$CH_2$—$CH_2$—$CH_2$— or —CH($CH_3$)—$CH_2$—;
$R^7$ is $C_1$–$C_{16}$-alkylene, $C_2$–$C_{16}$-alkenylene or a radical of a dimerized fatty acid;
x is 1 to 6, where the radicals $R^2$ and $R^3$ are identical or different when x is 2 to 6;
y is 0 or 1; and
z is 8 to 18, where the radicals B are identical or different.

14. The food composition defined in claim 13, further comprising at least one vitamin or carotenoid which is insoluble or virtually insoluble in water.

15. An ester of a hydroxylated carboxylic acid of formula Ia

wherein the substituents and variables independently of one another have the following meanings:

$R^1$ is hydrogen, $C_{12}$–$C_{22}$-acyl or a moiety

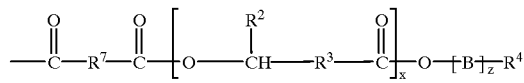

$R^2$ is $C_1$–$C_9$-alkyl;
$R^3$ is $C_6$–$C_{12}$-alkylene;
$R^4$ is methyl or ethyl;
$R^7$ is a radical of a dimerized fatty acid;
B is —$CH_2$—$CH_2$—O—;
x is 1 or 2, where the radicals $R^2$ and $R^3$ are identical or different when x is 2;
z is 10 to 18, where the radicals B are identical or different.

16. The ester of of formula Ia defined in claim 15, wherein
$R^1$ is hydrogen;
$R^2$ is $C_6$–$C_9$-alkyl;
$R^3$ is $C_9$–$C_{12}$-alkylene;
$R^4$ is methyl;
B is —$CH_2$—$CH_2$—O—;
x is 1 or 2, where the radicals $R^2$ and $R^3$ are identical or different when x is 2;
z is 10 to 18, where the radicals B are identical or different.

17. The ester of formula Ia defined in claim 15 which is represented by formula II

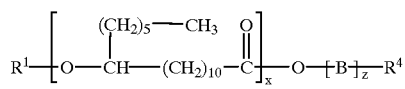
II wherein the substituents and variables independently of one another have the following meanings:
$R^1$ is hydrogen, $C_{12}$–$C_{22}$-acyl or a moiety

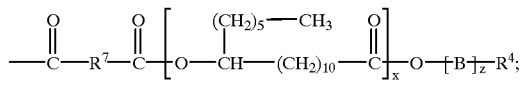

$R^4$ is methyl;

$R^7$ is a radical of a dimerized fatty acid;
B is —$CH_2$—$CH_2$—O—;
x is 1 or 2, where the radicals $R^2$ and $R^3$ are identical or different when x is 2;
z is 10 to 18, where the radicals B are identical or different.

18. An aqueous composition comprising as a solubilizer an effective amount of at least one compound of formula I

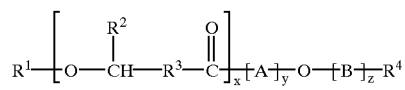
I wherein the substituents and variables independently of one another have the following meanings:
$R^1$ is hydrogen, $C_1$–$C_{22}$-acyl or a moiety

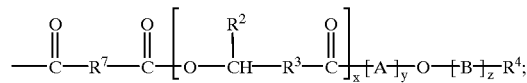

$R^2$ is hydrogen, $C_1$–$C_{16}$-alkyl or $C_2$–$C_{12}$-alkenyl;
$R^3$ is $C_1$–$C_{16}$-alkylene or $C_2$–$C_{16}$-alkenylene;
$R^4$ is $C_1$–$C_{12}$-alkyl, $C_2$–$C_{12}$-alkenyl or $C_1$–$C_{12}$-acyl;
A is —N($R^5$)—$R^6$—;
B is —$CH_2$—$CH_2$—O—, —$CH_2$—$CH_2$—$CH_2$—O— or —CH($CH_3$)—$CH_2$—O—;
$R^5$ is hydrogen, $C_1$–$C_{12}$-alkyl, $C_2$–$C_{12}$-alkenyl, $C_1$–$C_{12}$-acyl or $[B]_z$—$R^4$;
$R^6$ is —$CH_2$—$CH_2$—, —$CH_2$—$CH_2$—$CH_2$— or —CH($CH_3$)—$CH_2$—;
$R^7$ is $C_1$–$C_{16}$-alkylene, $C_2$–$C_{16}$-alkenylene or a radical of a dimerized fatty acid;
x is 1 to 6, where the radicals $R^2$ and $R^3$ are identical or different when x is 2 to 6;
y is 0 or 1; and
z is 8 to 18, where the radicals B are identical or different.

* * * * *